United States Patent
Lee et al.

(10) Patent No.: US 9,994,875 B2
(45) Date of Patent: Jun. 12, 2018

(54) RECOMBINANT STRAIN FOR PRODUCING 2,3-BUTANEDIOL, COMPRISING (A) INACTIVATED LACTATE DEHYDROGENASE AND (B) INACTIVATED SUCROSE REGULATOR

(71) Applicant: INDUSTRY-UNIVERSITY COOPERATION FOUNDATION SOGANG UNIVERSITY, Seoul (KR)

(72) Inventors: Jin Won Lee, Seoul (KR); Min Kyu Oh, Seoul (KR); Moo Young Jung, Seoul (KR)

(73) Assignee: INDUSTRY-UNIVERSITY COOPERATION FOUNDATION SOGANG UNIVERSITY, Seoul (KR)

(*) Notice: Subject to any disclaimer, the term of this patent is extended or adjusted under 35 U.S.C. 154(b) by 97 days.

(21) Appl. No.: 14/785,607

(22) PCT Filed: Jan. 23, 2014

(86) PCT No.: PCT/KR2014/000677
§ 371 (c)(1),
(2) Date: Oct. 19, 2015

(87) PCT Pub. No.: WO2014/116042
PCT Pub. Date: Jul. 31, 2014

(65) Prior Publication Data
US 2016/0186216 A1    Jun. 30, 2016

(30) Foreign Application Priority Data

Jan. 25, 2013   (KR) .................. 10-2013-0008816
Jul. 16, 2013   (KR) .................. 10-2013-0083817

(51) Int. Cl.
| | | |
|---|---|---|
| C12P 7/04 | (2006.01) | |
| C12N 9/04 | (2006.01) | |
| C07K 14/00 | (2006.01) | |
| C12N 1/20 | (2006.01) | |
| C12Q 1/68 | (2018.01) | |
| C12P 7/18 | (2006.01) | |
| C07K 14/26 | (2006.01) | |
| C12N 15/00 | (2006.01) | |
| C07K 14/245 | (2006.01) | |

(52) U.S. Cl.
CPC .............. *C12P 7/18* (2013.01); *C07K 14/245* (2013.01); *C07K 14/26* (2013.01); *C12N 9/0006* (2013.01); *C12N 15/00* (2013.01); *C12Y 101/01027* (2013.01)

(58) Field of Classification Search
None
See application file for complete search history.

(56) References Cited

U.S. PATENT DOCUMENTS

2010/0112655 A1   5/2010   Paul .............................. 435/160

FOREIGN PATENT DOCUMENTS

KR   10-2014-0038250   3/2014   ............. D06F 37/24

OTHER PUBLICATIONS

Jung. Deletion of lactate dehydrogenase in Enterobacter aerogenes to enhance 2,3-butanediol production. Appl Microbiol Biotechnol. Jul. 2012;95(2):461-9. doi: 10.1007/s00253-012-3883-9.*
Jung. Engineered Enterobacter aerogenes for efficient utilization of sugarcane molasses in 2,3-butanediol production. Bioresource Technology 139 (2013) 21-27.*
Jung. Alleviation of carbon cataboliterepression in Enterobacter aerogenes for efficient utilization of sugarcane molasses for 2,3-butanediol production. Biotechnol Biofuels (2015) 8:106.*
International Search Regort (ISR) dated May 16, 2014 in PCT/KR2014/000677.
Jung, S.-G., et al., (2012). "Removal of pathogenic factors from 2,3-butanediol-producing *Klebsiella* species by inactivating virulence-related wabG gene." *Appl. Microbiol. Biotechnol.* 97:1997-2007. See the entire document, especially abstract, figure 8.
Reid, S.J., et al., (2005). "Sucrose utilisation in bacteria: genetic organisation and regulation". *Appl. Microbiol. Biotechnol.* 67:312-321.

* cited by examiner

*Primary Examiner* — Yong D Pak
(74) *Attorney, Agent, or Firm* — Harness, Dickey & Pierce, P.L.C.

(57) ABSTRACT

The present invention relates to a recombinant strain for producing 2,3-butanediol, comprising (a) an inactivated lactate dehydrogenase and (b) an inactivated sucrose regulator. According to the present invention, it is possible to economically produce 2,3-butanediol using a cheap carbon source, and the efficiency and productivity of 2,3-butanediol is remarkable compared with a wild type.

7 Claims, 7 Drawing Sheets

RECOMBINANT STRAIN FOR PRODUCING 2,3-BUTANEDIOL, COMPRISING (A) INACTIVATED LACTATE DEHYDROGENASE AND (B) INACTIVATED SUCROSE REGULATOR

CROSS-REFERENCE TO RELATED APPLICATIONS

This application is a national phase application of PCT Application No. PCT/KR2014/000677, filed on 23 Jan. 2014, which claims benefit of Korean Patent Application No. KR 10-2013-0083817, filed on 16 Jul. 2013, which claims benefit of Korean Patent Application No. KR 10-2013-0008816, filed on 25 Jan. 2013. The entire disclosure of the applications identified in this paragraph is incorporated herein by reference.

FIELD

The present invention was made with the support of the Ministry of Knowledge Economy, Republic of Korea, under Project No. 10035578, which was conducted in the program titled "Industrial Technology Development Business" in the project named "Identification of 2,3-Butanediol Producing Strains and Development of Metabolic Pathway Optimization Technology" by the Industry-Academic Cooperation Foundation, SOGANG University, under management of the Korea Evaluation Institute of Industrial Technology, during the period of 1 Apr. 2010 to 31 Mar. 2015.

The present invention relates to a recombinant strain for producing 2,3-butanediol, including (a) an inactivated lactate dehydrogenase, and (b) an inactivated sucrose regulator.

BACKGROUND

The development of the biorefinery industry has enabled and improved the eco-friendly production of several industrial chemicals with a reduced dependency on petroleum resources. As an example, the microbial production of 2,3-butanediol as a platform chemical has attracted great interests, due to its large potential in industrial applications (Ji et al., 2011). Therefore, several bacterial species, such as *Klebsiella pneumonia* (Ma et al., 2009), *Serratia marcescens* (Zhang et al., 2010) and *Enterobacter aerogenes* (Jung et al., 2012), have been developed as industrial strains for 2,3-butanediol production.

The price of the carbon source accounts for a large portion of the cost of microbial 2,3-butanediol production. Therefore, there have been many efforts to find cheap substrates. Sun et al. (2009) reported that *Klebsiella pneumoniae* produced 91.63 g/L of 2,3-butanediol from pretreated Jerusalem artichoke tubers by fedbatch simultaneous saccharification and fermentation (SSF). Wang et al. (2010) used corncob molasses, a waste byproduct in xylitol production, for 2,3-butanediol production, where 78.9 g/L of 2,3-butanediol was produced by *K. pneumonia* after 61 h of fed-batch fermentation. Jiang et al. (2012) tried to produce 2,3-butanediol from acid hydrolysates of jatropha hulls, where a two-step hydrolysis was applied to effectively hydrolyze the jatropha hulls, and 31.41 g/L of 2,3-butanediol was achieved by *Klebsiella oxytoca*.

In 2008, the USDA reported that the price of sugarcane molasses was less than $0.50/kg (Chan et al., 2012). Sugarcane molasses contains a few mixed sugars, a dominant amount of sucrose, and similar amounts of glucose and fructose (Akaraonye et al., 2012). Therefore, the efficient utilization of sucrose is necessary in order to maximize the use of sugarcane molasses. A sucrose utilization pathway has been studied in enteric bacteria. As shown in FIG. 1a, the transport and catabolism of sucrose can be classified into two routes: the phosphotransferase system (PTS) and non-PTS (Reid and Abratt, 2005). A PTS-dependent transporter imports sucrose with phosphorylation by Ellscr, which was characterized in *K. pneumonia* as scr operon (Sprenger and Lengeler, 1988). Meanwhile, a non-PTS permease transfer of sucrose into the cell without chemical modification has been determined in *Escherichia coli* as csc operon (Bockmann et al., 1992). In *K. pneumonia*, the operon consisted of five open reading frames, encoding fructokinase (ScrK), sucrose-specific outer membrane porin (ScrY), PTS EII transport protein (ScrA), sucrose-6-phophate hydrolase (ScrB) and sucrose dependent regulator (ScrR) (FIG. 1b). The transcription of scr operon was repressed by ScrR. However, the effect of scrR mutation on the utilization of sugarcane molasses has not been reported yet.

SUMMARY

The present inventors have endeavored to develop a strain and a carbon source, capable of reducing production costs of 2,3-butanediol. As a result, the present inventors have verified that, when a recombinant strain including an inactivated lactate dehydrogenase and an inactivated sucrose regulator is cultured in a culture medium containing molasses as a carbon source, the recombinant strain shows excellent production efficiency of 2,3-butanediol, and thus have completed the present invention.

Therefore, an aspect of the present invention is to provide a recombinant strain for producing 2,3-butanediol.

Another aspect of the present invention is to provide a method for producing 2,3-butanediol.

Still another aspect of the present invention is to provide 2,3-butanediol.

Other purposes and advantages of the present disclosure will become more obvious with the following detailed description of the invention, claims, and drawings.

According to an aspect of the present invention, the present invention provides a recombinant strain for producing 2,3-butanediol, comprising (a) an inactivated lactate dehydrogenase, and (b) an inactivated sucrose regulator.

The present inventors have endeavored to develop a strain and a carbon source, capable of reducing production costs of 2,3-butanediol. As a result, the present inventors have verified that, when a recombinant strain including an inactivated lactate dehydrogenase and an inactivated sucrose regulator is cultured in a culture medium containing molasses as a carbon source, the recombinant strain shows excellent production efficiency of 2,3-butanediol.

The basic scheme of the present invention is to inactivate a lactate dehydrogenase and a sucrose regulator, which are found in 2,3-butanediol producing strains. The lactate dehydrogenase, which is triosephosphate isomerase, is an enzyme to catalyze the conversion of pyruvate into lactate by reducing nicotinamide adenine dinucleotide (NADH) in the glycolysis. The sucrose regulator, which is one of LacI-GalR family members, is a transcriptional suppressor that suppresses the expression of ScrB encoding a sucrose hydrolase, and has the same meaning as a sucrose operon repressor and a LacI family transcriptional regulator.

A lactate dehydrogenase and a sucrose regulator, which are targets of inactivation, have been found and identified in various strains. Examples below show a lactate dehydrogenase of *Enterobacter aerogenes* of SEQ ID NO: 1 and a sucrose regulator of *Enterobacter aerogenes* of SEQ ID NO: 2, but besides, various lactate dehydrogenases and sucrose regulators are included in the present invention. For example, lactate dehydrogenases disclosed in GenBank Accession No. CP_002824 (*Enterobacter aerogenes*), GenBank Accession No. NC_015663 (*Enterobacter aerogenes*), GenBank Accession No. NC_018522 (*Klebsiella pneumonia*), GenBank Accession No. NC_011283 (*Klebsiella pneumoniae*), GenBank Accession No. NC_017540 (*Klebsiella pneumoniae*), GenBank Accession No. NC_012731 (*Klebsiella pneumoniae*), GenBank Accession No. NC_016612 (*Klebsiella oxytoca*), and GenBank Accession No. NC_018106 (*Klebsiella oxytoca*) may be targets of inactivation in the present invention, and sucrose regulators disclosed in GenBank Accession No. CP_002824 (*Enterobacter aerogenes*), GenBank Accession No. NC_015663 (*Enterobacter aerogenes*), GenBank Accession No. NC_01852 (*Klebsiella pneumoniae*), GenBank Accession No. NC_011283 (*Klebsiella pneumoniae*), GenBank Accession No. NC 016612 (*Klebsiella oxytoca*), and GenBank Accession No. NC_018106 (*Klebsiella oxytoca*) may be targets of inactivation in the present invention.

As used herein to refer to the lactate dehydrogenase and sucrose regulator, the term "inactivation" means the inclusion of all mutations (e.g., deletion, substitution, or insertion) that cause the loss of functions of the lactate dehydrogenase and the sucrose regulator. For example, the deletion in the lactate dehydrogenase gene and the sucrose regulator gene includes all of a partial deletion and a total deletion in the dehydrogenase gene or the sucrose regulator gene.

According to an embodiment of the present invention, the inactivated lactate dehydrogenase has a deletion, substitution, or insertion mutation occurring in the nucleotide sequence encoding a lactate dehydrogenase.

According to an embodiment of the present invention, the inactivated sucrose regulator has a deletion, substitution, or insertion mutation occurring in the nucleotide sequence encoding a sucrose regulator.

The mutation in the sequence encoding the lactate dehydrogenase or sucrose regulator may be induced by various mutagenesis methods known in the art. The mutation to inactivate the lactate dehydrogenase or sucrose regulator may be induced by, for example, PCR mutagenesis, cassette mutagenesis (Sambrook, J. et al., Molecular Cloning. A Laboratory Manual, 3rd ed. Cold Spring Harbor Press (2001)), A Red recombination (Jung et al., 2012; Datsenko and Wanner, Proc. Natl. Acad. Sci. USA, 97: 6640-6645, 2000), Rac phage RecE/RecT system (Zhang et al., Nature Biotechnol., 18:1314-1317, 2000), FLP-FRT recombination (Zhu X D, Sadowski P D (1995) "Cleavage-dependent Ligation by the FLP Recombinase". Journal of Biological Chemistry 270 (39): 23044-54), site-specific recombination (Sauer, Brian; Henderson, Nancy (1988). "Site-Specific DNA Recombination in Mammalian Cells by the Cre Recombinase of Bacteriophage P1". Proceedings of the National Academy of Sciences of the United States of America 85 (14): 5166-70), Cre-Lox recombination (Turan, S.; Galla, M.; Ernst, E.; Qiao, J.; Voelkel, C.; Schiedlmeier, B.; Zehe, C.; Bode, J. (2011). "Recombinase-mediated cassette exchange (RMCE): traditional concepts and current challenges". J. Mol. Biol. 407 (2): 193-221), chromosome crossing (Creighton H, McClintock B (1931). "A Correlation of Cytological and Genetical Crossing-Over in *Zea Mays*". Proc Natl Acad Sci USA 17 (8): 492-7), and transposon (US 20090305369).

According to another embodiment of the present invention, the inactivated lactate dehydrogenase has a deletion mutation occurring in the nucleotide sequence encoding a lactate dehydrogenase.

According to another embodiment of the present invention, the inactivated sucrose regulator has a deletion mutation occurring in the nucleotide sequence encoding a sucrose regulator.

According to a specific embodiment of the present invention, the deletion mutation is induced by the A Red recombination.

The recombinant strain for producing 2,3-butanediol, including (a) an inactivated lactate dehydrogenase, and (b) an inactivated sucrose regulator, of the present invention, may be additionally subjected to genetic engineering in order to remove pathogenicity when applied to pathogenic strains.

According to an embodiment of the present invention, the recombinant strain for producing 2,3-butanediol has a deletion, substitution, or insertion mutation that additionally occurs in the nucleotide sequence encoding wabG. According to another embodiment of the present invention, the deletion mutation occurs in the nucleotide sequence encoding wabG.

The recombinant strain for producing 2,3-butanediol, including (a) an inactivated lactate dehydrogenase, and (b) an inactivated sucrose regulator, of the present invention, may be applied to various strains for producing 2,3-butanediol.

According to an embodiment of the present invention, the strain is *Aeromonas* sp., *Bacillus* sp., *Brevibacillus* sp., *Corynebacterium* sp., *Enterobacter* sp., *Klebsiella* sp., *Lactobacillus* sp., *Lactococcus* sp., *Leuconostoc* sp., *Oenococcus* sp., *Pediococcus* sp., *Raoultella* sp., *Serratia* sp., *Streptococcus* sp., or *Rhizobacterium* sp.; according to another embodiment of the present invention, the strain is *Enterobacter* sp., or *Klebsiella* sp.; and according to a specific embodiment of the present invention, the strain is *Enterobacter aerogenes* or *Krebsiella pneumonia*.

The strain for producing 2,3-butanediol of the present invention uses sugar-cane molasses as a carbon source.

According to a specific embodiment of the present invention, when the strain for producing 2,3-butanediol of the present invention is cultured in a culture medium containing sugar-cane molasses as a carbon source, the strain exhibits superior 2,3-butanediol efficiency and productivity compared with when the strain is cultured in a culture medium containing glucose or other carbon source (e.g., fructose or sucrose).

According to another embodiment of the present invention, provided is a method for producing 2,3-butanediol, the method including culturing the strain of the present invention in a culture medium.

In the method for producing 2,3-butanediol of the present invention, the medium in the culturing step includes any medium that is used to culture the *Enterobacter* strain, and contains a carbon source, a nitrogen source, and an energy source.

The carbon source used in the method of the present invention may employ various carbohydrates. According to an embodiment of the present invention, the carbon source is molasses, glucose, sucrose, or fructose, and according to another embodiment of the present invention, the carbon source is molasses. The nitrogen source used in the method of the present invention may employ an organic nitrogen source. According to an embodiment of the present invention, the nitrogen source is a yeast extract and peptones, and according to another embodiment of the present invention, the nitrogen source is a yeast extract. The energy source used in the method of the present invention employs both a carbon source and a nitrogen source.

The culture medium may further contain trace element sources and essential amino acid sources, in addition to the carbon source, the nitrogen source, and the energy source. According to an embodiment of the present invention, the trace element sources include KCl, $(NH_4)SO_4$, $Na_2SO_4$, $MgSO_4.7H_2O$, $ZnCl_2$, $FeCl_3.6H_2O$, $MnCl_2.4H_2O$, $CuCl_2.2H_2O$, and $H_3BO_3$, and the essential amino acid sources include casamino acid.

The pH of the sugar cane molasses used as a carbon source in the present invention is very low, pH 4.94, and thus the pH needs to be adjusted for the normal growth of strains during the culturing procedure. According to an embodiment of the present invention, the culture medium has an optimal pH range of pH 5.5 to pH 7.0.

In the culturing step of the present invention, the culture temperature is 30° C. to 40° C.; according to an embodiment of the present invention, the culture temperature is 33° C. to 39° C.; and according to another embodiment of the present invention, the culture temperature is 35° C. to 38° C.

The method for producing 2,3-butanediol of the present invention is performed through various methods of culturing the recombinant strain of the present invention.

According to an embodiment of the present invention, the culturing is performed by bath fermentation or fed-batch fermentation.

As used herein, the term "batch fermentation" refers to a fermentation using only the initial medium without adding or removing a medium during the fermentation, and the term "fed-batch fermentation" refers to fermentation with adding or removing a medium during the fermentation.

According to a specific embodiment of the present invention, in cases where the method for producing 2,3-butanediol of the present invention is performed by bath fermentation, the 2,3-butanediol efficiency is 0.329 g/g of sugar, exhibiting an improvement by 10% or higher compared with culturing of wild-type strains, and the 2,3-butanediol productivity is 2.14 g/l/h, exhibiting an improvement by 60% or higher compared with culturing of wild-type strains; and in cases where the method is performed by fed-batch fermentation, the 2,3-butanediol efficiency is 0.359 g/g of sugar, and the 2,3-butanediol productivity is 2.02 g/l/h.

According to still another aspect of the present invention, the present invention provides 2,3-butanediol produced by the method of the present invention.

As used herein, the term "2,3-butanediol efficiency" refers to the 2,3-butanediol production per g of sugar added in the medium as a carbon source, and the term "2,3-butanediol productivity" refers to 2,3-butanediol produced in 1 L for 1 h.

Since 2,3-butanediol of the present invention is directed to 2,3-butanediol produced by the production method, descriptions of overlapping contents there between are omitted to avoid excessive complexity of the specification due to repetitive descriptions thereof.

BRIEF DESCRIPTION OF THE DRAWINGS

The above and other objects, features and advantages of the present invention will be more apparent from the following detailed description taken in conjunction with the accompanying drawings, in which:

FIGS. 5a, 5b, 5c, and 5d show flask culture results using, a sole carbon source, glucose, fructose, sucrose, and molasses, respectively.

DETAILED DESCRIPTION

Figure 1A:
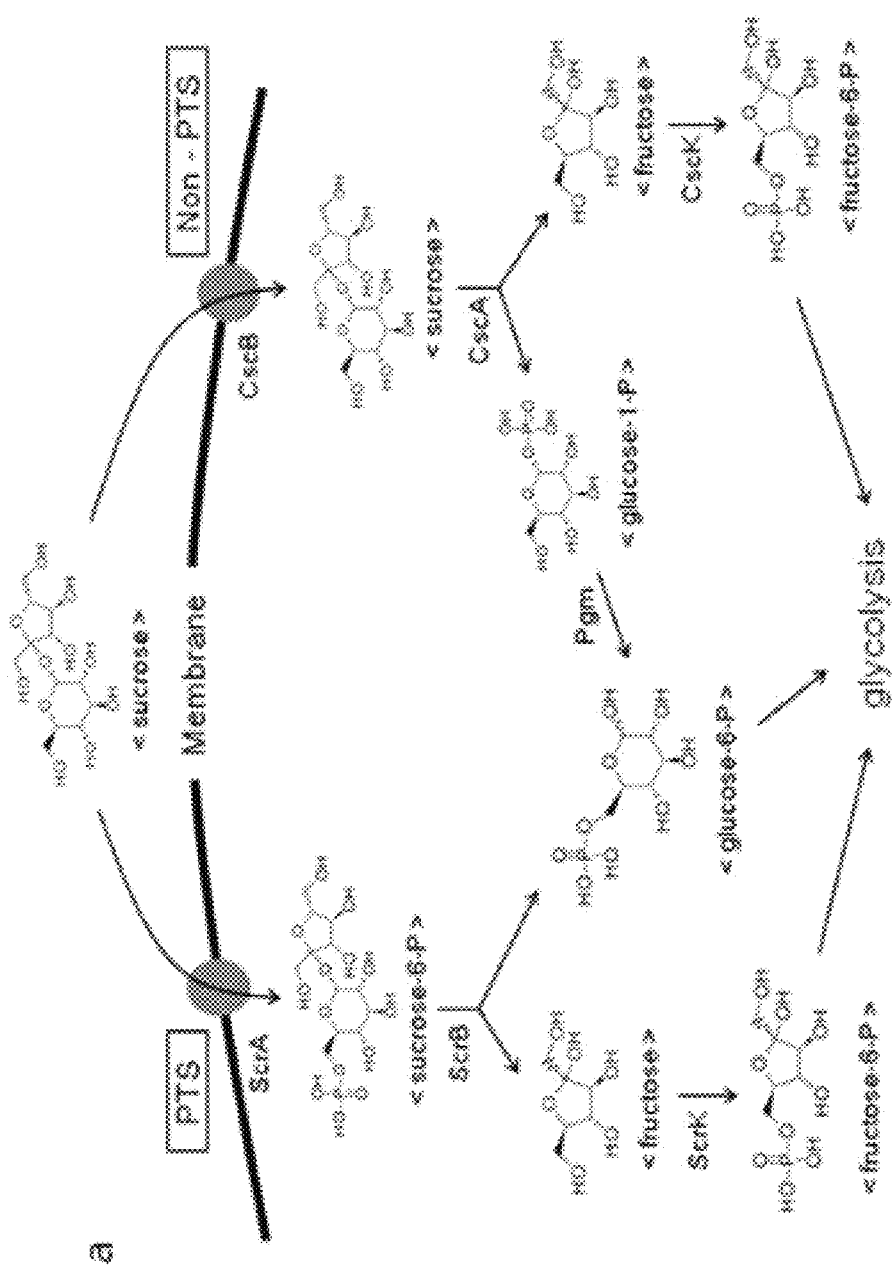
FIGS. 1a to 1b are diagrams showing (a) Bacterial sucrose catabolic pathways with PTS and non-PTS sugar transporters and (b) the corresponding gene arrangements in the genome of three enteric bacteria. ScrA, EII transport protein for sucrose; CscB, sucrose-specific permease; ScrB and CscA, sucrose-6-phosphate hydrolase; ScrK and CscK, fructokinase; Pgm, phospoglucomutase; ScrY, outer membrane sucrose porin; ScrR and CscR, repressors of the sucrose metabolic genes.
Figure 1B:
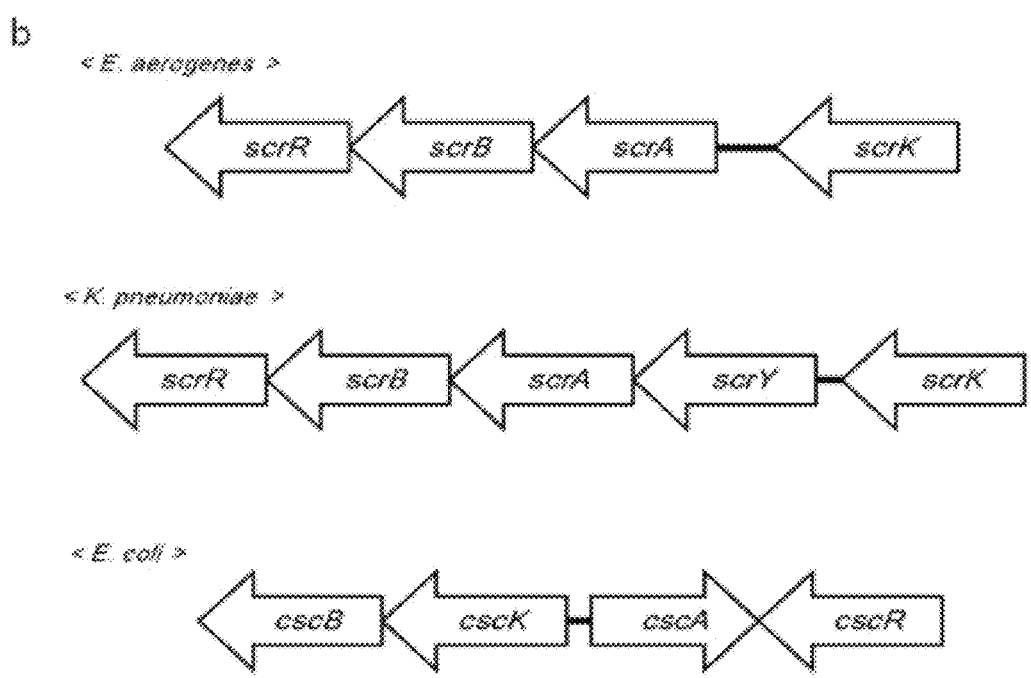

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1: 2,3-Butanediol Production Using *Enterobacter aerogenes*

1. Experimental Materials & Methods
1.1 Strain Development

All *E. aerogenes* strains were derived from a wild type strain, KCTC 2190. Previously, a k Red recombination method for *E. aerogenes* was used for deleting a lactate dehydrogenase (LdhA) from KCTC 2190, generating EMY-01 (Jung et al., 2012). In this study, the gene encoding sucrose regulator of the LacI family, ScrR, was deleted in the genome of EMY-01 in a similar manner, and the resulting strain was named EMY-68. The scrR_FKF_fw and scr-R_FKF_ry primers were used for the deletion, which was confirmed by the colony PCR with the primers scrR_con_A and scrR_con_B. The strains, plasmids, or primers used in this study are listed in Table 1. In order to remove scrR gene of *Enterobacter aerogenes*, the λ Red recombination method was employed. First, *Enterobacter aerogenes*, prepared as competent cells, was transformed with expression vectors of exo, gamma, and beta for preventing the degradation of the liner gene introduced into cells and increasing the efficiency of homologous recombination. pKM208 vector which has a tac promoter and ampicillin resistance was used in the present invention, and the transformation was verified. Next, a linear gene for homologous recombination was created. pKD4 vector having a FRT-kanamycin-FRT cassette was used as a template. Primers were manufactured using a total of 70 nucleotide pairs containing 50 nucleotide pairs that are homologous at both sides of the scrR gene of *Enterobacter aerogenes*, at which homogenous combination occurs, and 20 nucleotide pairs for polymerizing the FRT-kanamycin-FRT cassette of pKD4 used as a template, and a linear gene for removing scrR gene was prepared using polymerase chain reaction. Kanamycin is an anti-drug for investigating whether or not the homogeneous combination successfully occurs, and the FRT site functions to remove an anti-drug for removing a different gene after the target gene is removed.

In the next step, *Enterobacter aerogenes*, which has been verified to be transformed with pKM208 vector, was cultured at 30° C. Since the pKM208 vector is temperature-sensitive and thus lose its activity at 37° C. or higher, the strain was cultured at 30° C. In addition, when the OD600 value is about 0.1 after the culturing for 1 h, the expression of the A Red recombinase of pKM208 was induced by 1 mM isopropylthio-β-galactoside (IPTG). When the OD600 value is about 0.6 by further culturing for 1 h, competent cells for electroporation was manufactured, and then the linear gene was transformed. After culturing in LB medium at 37° C. for 1 h, the cells were spread on LB solid medium supplemented with 12.5 mg/mQ kanamycin, and then cultured for 12 h. In order to investigate whether the homogeneous combination is successful, two primers were manufactured. 20-24 nucleotide pairs that are homogenous at both sides of the lactate dehydrogenase were named scrR_con_A and _B. These two primers were used to perform colony PCR, thereby investigating whether the homogenous recombination occurred or not, through the length of PCR products.

TABLE 1

| Strains, plasmids or primers | Genotype, relevant characteristics or sequence | Source and references |
|---|---|---|
| Strains | | |
| E. aerogenes KCTC 2190 | Wild type | Korean Collection for Type Culture |
| EMY 01 | E. aerogenes KCTC 2190-ΔldhA | (Jung et al., 2012) |
| EMY 68 | E. aerogenes KCTC 2190 ΔldhA ΔscrR | This study |
| Plasmids | | |
| pKM208 | lacI, λ Red + Gam-producing vector, tac_promoter, f1_ori, Amp$^R$ | Addgene |
| pCP20 | FLP recombinase producing vector, pSC101 ori, cI857, Amp$^R$, Cm$^R$ | (Datsenko & Wanner, 2000) |
| pKD4 | FRT flanked resistance cassette involved vector, oriRγ, Km$^R$ | (Datsenko & Wanner, 2000) |
| Primers | | |
| scrR_FKF_fw$^a$ | CGGCCATGCATGGTAGAATAAG CGTTTTGCTTTCAGGC GCCTGTCTCGTGGTGTAGGCTG GAGCTGCTTC (SEQ ID No. 3) | This study This study |

TABLE 1 -continued

| Strains, plasmids or primers | Genotype, relevant characteristics or sequence | Source and references |
|---|---|---|
| scrR_FKF_rv$^a$ | GACAATTAACCG TTAACAGTACGGGCCTGAACCA CGATCCAGGCCCGTTA TCCTCCTTAGTTCCTATTCC (SEQ ID No. 4) | This study |
| scrR_con_A | CCGCTTCTTTGCGGATTAT (SEQ ID No. 5) | |
| scrR_con_B | GCGCTCATTCATGAAAAATTC (SEQ ID No. 6) | This study |

$^a$Underlined sequences are the homologous sequence with scrR of *E. aerogenes*.

1.2. Media and Culture Conditions

The fermentation medium contained (g/L): 3 g $KH_2PO_4$, 6.8 g $Na_2HPO_4$, 0.75 g KCl, 0.35 g $(NH_4)_2SO_4$, 0.28 g $Na_2SO_4$, 0.26 g $MgSO_4.7H_2O$, 0.42 g citric acid, 5 g yeast extract, 10 g casamino acid and 0.3 ml microelement solution containing 34.2 g/L $ZnCl_2$, 2.7 g/L $FeCl_3\ 6H_2O$, 10 g/L $MnCl_2\ 4H_2O$, 0.85 g/L $CuCl_2\ 2H_2O$, and 0.31 g/L $H_3BO3$, as described previously (Jung et al., 2012). In a flask culture, 60 g/L of the individual sugars: glucose, fructose, sucrose, or sugarcane molasses, were additionally added to the medium as the sole carbon source. Glucose, fructose, sucrose and all other compositions of medium were purchased from Sigma (St. Louis, Mo., USA). A Brazilian sugarcane molasses was used, the specific details of which are presented in Table 2, and its measured sugar contents were 87 g/L fructose, 81 g/L glucose, and 387 g/L sucrose. Differently from the media containing other carbon sources (pH 6.8), the pH of the medium with sugarcane molasses was low, so that it adjusted to above 6.2 by addition of 5 M NaOH. The flask sealed with silicon stopper was incubated at 37° C. and 250 rpm in a 250 ml flask containing 50 ml media for 12 h.

TABLE 2

| Composition | Portion |
|---|---|
| Total sugars | 57.02% |
| Non fermentative sugars | below 4% |
| N | 0.5-1.5% |
| $P_2O_5$ | 0.1-0.4% |
| Ash | below 15% |
| pH | 4.94 |
| Sludge | below 0.71% |
| Country of origin | Brazil |

The batch and fed-batch fermentations were carried out in a 5 L stirred bioreactor (Bio Control and System, Daejeon, Korea) containing 3 L of fermentation medium with 5% (v/v) inoculum. The operating temperature, agitation speed, and air flow were maintained at 37° C., 280 rpm, and 1.5 wm, respectively. All fermentation processes were initiated at pH 6.8, and were then maintained at pH 6.0 by the automatic addition of 5 M NaOH. Antifoam 204 (Sigma) was used when needed. Batch fermentations were carried out with 80 g/L of sugar cane molasses, as indicated in the results and discussion section. The total sugar concentration of fed-batch fermentations was maintained under 60 g/L by feeding sterilized sugar cane molasses.

1.3. Analytical Methods

The metabolites, as obtained from flask and fermentation cultures, were analyzed by high performance liquid chromatography (Waters HPLC 1500 series, MA, USA) equipped with a RI detector at 45_C. Organic acids, 2,3- butanediol, acetoin, and ethanol were measured using Sugar SH1011 column (Shodex, Tokyo, Japan) at 75° C. and 10 mM sulfuric acid was used as the mobile phase. Fructose, glucose, and sucrose were determined using High Performance Carbohydrate Column (Waters) at 35° C. and 80% acetonitrile was used as the mobile phase. The flow rate of both mobile phases was 0.5 ml/min.

Cell growth was monitored by a measurement of optical density at 600 nm (OD600) with a UV-Vis spectrophotometer (Shimadzu UV mini 1240, Tokyo, Japan).

2. Results and Discussion 2.1. Carbon Sources Effects on *E. aerogenes* Mutants in Flask Culture The gene cluster for sucrose catabolism in *K. pneumonia* is repressed by a sucrose regulator of the LacI family, ScrR (Reid and Abratt, 2005). Therefore, the knockout of scrR gene was expected to improve sucrose utilization. The scrR gene was searched for in the *E. aerogenes* KCTC 2190 genome (Shin et al., 2012) using BLAST (Basic Local Alignment Search Tool) with the sequence of ScrR protein of *K. pneumonia* (Mortlock, 1982). A 92% homolog in protein sequence was found in *E. aerogenes*. As listed in Table 1, the primers were designed and scrR gene was successfully deleted from the genomic DNA (data not shown).

Flask cultivations of wild type KCTC 2190, EMY-01, and EMY-68 were performed with 60 g/L of various carbon sources such as glucose, fructose, sucrose, and sugarcane molasses for 12 h to confirm the effect of scrR deletion. In our previous study, EMY-01, the lactate dehydrogenase deletion mutant, had showed enhanced utilization of several carbon sources compared to its parent strain (Jung et al., 2012). Similar to the previous results, the consumption of carbon sources, cell growth, 2,3-butanediol production, yield, and productivity of EMY-01 were significantly increased compared to those of the wild type strain in all four carbon sources (Table 3).

Figure 2:
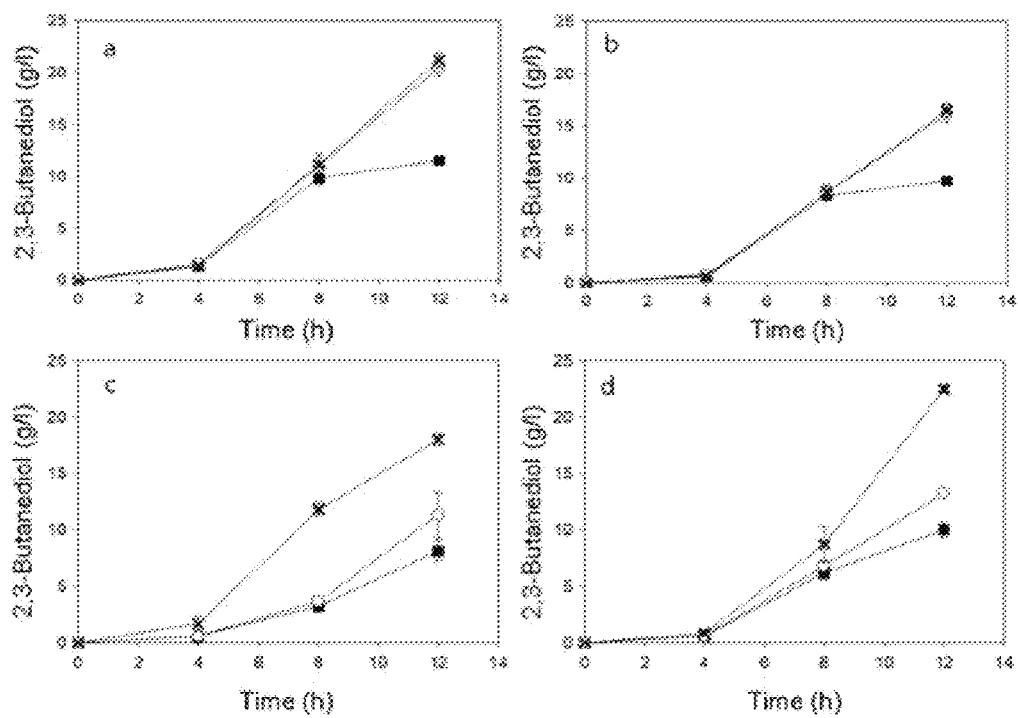
FIGS. 2a to 2d show graph for 2,3-Butanediol production of wild type (closed squares), EMY-01 (open circles), and EMY-68 (crosses) in flask cultivation with (a) glucose, (b) fructose, and (c) sucrose, or (d) sugarcane molasses as a sole carbon source. Error bars represent the standard deviations of three experiments.

As shown in FIGS. 2a and b, EMY-68 had a phenotype almost identical to EMY-01 when grown in glucose and fructose, suggesting that the disruption of scrR did not affect the consumption of these carbon sources. However, the growth and 2,3-butanediol production of EMY-01 were not significantly improved in sucrose and molasses compared to the wild type, while EMY-68 showed a much improved sucrose utilization and 2,3-butanediol production than its parent strain (FIGS. 2c and d). EMY-68 produced 18.05 g/L 2,3-butanediol and consumed 57.65 g/L sucrose in 12 h, representing increases of 59.6% and 41.9%, respectively, compared to that of EMY-01. Higher improvements were observed with sugarcane molasses, showing 2,3-butanediol production and consumption of carbon sources of EMY-68 increased by 69.9% and 44.6%, respectively, compared to those of EMY-01 (Table 3).

Although sucrose is a dimer of glucose and fructose, scrR deletion only influenced sucrose metabolism, and not that of fructose. For fructose utilization in *E. aerogenes*, extracellular fructose is taken up by a multicomponent phosphotransferase system (PTS) and is converted into intracellular fructose-1-phosphate (Ferenci and Kornberg, 1973; Kelker et al., 1970). Fructose-1-phosphate is then phosphorylated to fructose-1,6-bisphoshate, which is subsequently consumed by glycolysis. On the other hand, the fructose moiety of sucrose is hydrolyzed and then converted to fructose-6-phosphate by fructokinase (FIG. 1a). Since ScrR was known to bind mainly to the intracellular fructose and to repress only the scr operon, scrR deletion could not affect the catabolism of fructose (Jahreis and Lengeler, 1993). The effect of sucrose regulator deletion on sucrose metabolism was qualitatively consistent with a previous report for *E. coli* (Arifin et al., 2011), which has a PTS non-dependent sucrose transporter. The effect of scrR deletion was also clearly observed when molasses was used as a carbon source, because sucrose is the main sugar in molasses.

In a flask culture with an economic carbon source, sugarcane molasses, 2,3-butanediol titer, yield, and productivity of IdhA and scrR double mutant increased by 124.7%, 27.6%, and 121.4%, respectively, compared to those of the wild type strain (Table 3). This result demonstrated the advantage of genetic engineering in utilizing an industrial feedstock such as molasses in biorefinery.

TABLES 3 AND 4

Comparison of optical density (OD600) and metabolite profiles obtained from wild type and its mutants using several carbon sources in a 12 h flask cultivation[a].

| Carbon source | Glucose | | | Fructose | | | Sucrose | | | Molasses | | |
|---|---|---|---|---|---|---|---|---|---|---|---|---|
| Strain | Wild type | EMY-01 | EMY-68 | Wild type | EMY-01 | EMY-68 | Wild type | EMY-01 | EMY-68 | Wild type | EMY-01 | EMY-68 |
| $OD_{600}$ | 11.73 | 17.7 | 18.2 | 13.18 | 16.58 | 16.88 | 10.27 | 11.97 | 15.17 | — | — | — |
| Consumption of sugars (g/L) | 39.19 | 62.00 | 61.91 | 35.58 | 51.31 | 51.43 | 31.94 | 40.62 | 57.65 | 33.83 | 41.77 | 60.42 |
| 2,3-BDO production (g/L) | 11.54 | 20.46 | 21.00 | 9.74 | 16.21 | 16.49 | 8.12 | 11.31 | 18.05 | 10.02 | 13.25 | 22.51 |
| 2,3-BDO yield (g/g/sugars) | 0.28 | 0.31 | 0.32 | 0.27 | 0.32 | 0.32 | 0.26 | 0.29 | 0.31 | 0.29 | 0.31 | 0.37 |
| 2,3-BDO productivity (g/L/h) | 0.96 | 1.70 | 1.75 | 0.81 | 1.35 | 1.37 | 0.68 | 0.94 | 1.50 | 0.84 | 1.10 | 1.86 |
| Acetoin (g/L) | 0.43 | 0.84 | 0.60 | 0.51 | 0.63 | 0.63 | 0.84 | 0.89 | 0.98 | 0.34 | 0.34 | 0.82 |
| Ethanol (g/L) | 6.00 | 10.46 | 10.38 | 4.50 | 7.10 | 7.30 | 4.03 | 5.94 | 9.21 | 6.08 | 6.47 | 12.76 |
| Lactate (g/L) | 4.66 | 0.69 | 0.56 | 3.67 | 0.80 | 0.46 | 0.44 | 0 | 0.77 | 1.06 | 0 | 0.01 |
| Succinate (g/L) | 2.11 | 3.30 | 3.58 | 2.79 | 3.58 | 3.69 | 3.86 | 4.30 | 3.25 | 0.21 | 0.51 | 1.29 |
| Initial pH | 6.73 | 6.73 | 6.73 | 6.85 | 6.85 | 6.85 | 6.86 | 6.86 | 6.86 | 6.14 | 6.14 | 6.14 |
| Final pH | 4.64 | 5.2 | 5.17 | 4.7 | 5.47 | 5.48 | 5.42 | 5.39 | 5.47 | 5.54 | 5.65 | 5.55 |

[a]The data were averages and standard deviations of three experiments.

Figure 3:
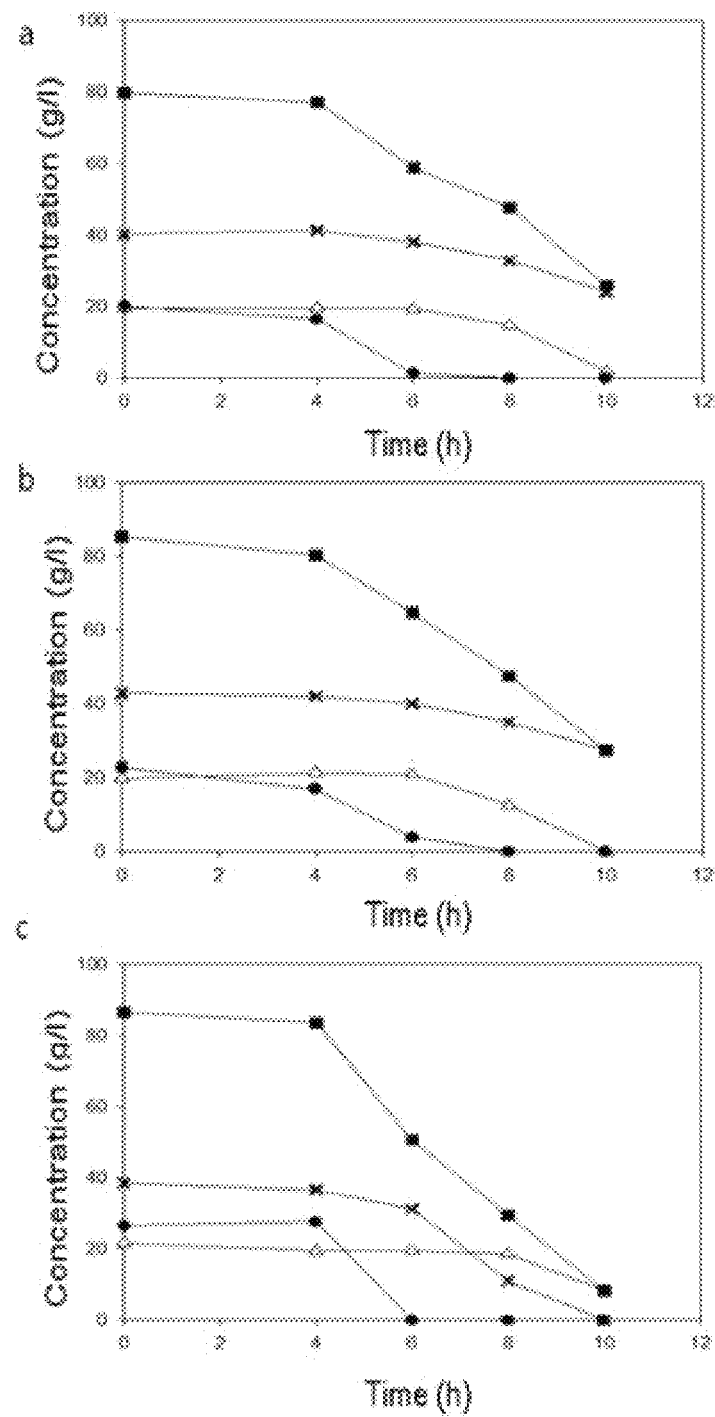
FIGS. 3a to 3c show graph for comparison of batch fermentations of (a) wild type, (b) EMY-01, and (c) EMY-68 with the consumption of sugars including glucose (closed circles), sucrose (crosses), fructose (open triangles) and total sugars (closed squares). Error bars represent the standard deviations of three experiments.

2.2 Effects of the Mutation on Batch Fermentation Using Sugarcane Molasses and on Sugar Utilization Preference Batch fermentation of wild type KCTC 2190, EMY-01, and EMY-68 was conducted at 80 g/L initial sugarcane molasses concentration for 10 h in a 5 L fermenter. The effects of IdhA and scrR deletions were similar to those in flask cultures with molasses. EMY-68 produced 28.88 g/L 2,3-butanediol, and consumed 82.13 g/L carbon (Table 4), which was significantly higher than that of wild type and EMY-01. In this experiment, the consumptions of main sugars in molasses, glucose, fructose, and sucrose, were monitored to find the effect of scrR deletion on carbon source utilization (FIG. 3). Glucose was the preferred carbon source for all three strains. After glucose was depleted, wild type and EMY-01 utilized fructose and sucrose at similar rates (FIGS. 3a and b). Since sucrose concentrations were much greater than fructose in sugarcane molasses, fructose was depleted earlier than sucrose. Meanwhile, EMY-68 consumed sucrose much faster than the wild type, and subsequently did fructose (FIG. 3c).

When provided with a mixture of several carbon sources, most bacteria generally consume carbon sources in a sequential manner (Bruckner and Titgemeyer, 2002; Goerke and Stulke, 2008; Stulke and Hillen, 1999). The use of preferred carbon sources represses or activates the activity of catabolic mechanisms that enable the utilization of secondary carbon sources. In E. aerogenes, all three sugars: glucose, fructose, and sucrose, are transferred across the cytoplasmic membrane by PTS. Therefore, a few possible mechanisms can be suggested for the change in carbon source preference. Firstly, the fru operon for fructose catabolism is regulated at a transcription level, mainly by catabolite repressor/activator protein (Cra, previously designated fruR) in E. coli (Saier and Ramseier, 1996). Recently, the Cra binding site was found on the promoter region of the csc operon encoding the genes for sucrose catabolism in E. coli (Sabri et al., 2013). Similarly, it is likely that Cra is involved in the regulation of the scroperon in E. aerogenes. When the scrR gene is eliminated, the transcription regulation of the scr operon by Cra can be perturbed and activated to a stronger degree than the fru operon upon glucose depletion. Secondly, the basal expression level of scr operon is enhanced by the deletion of scrR, resulting in a higher expression of ScrA compared to the fructose transporter. This enhanced the activation of scr operon over the fru operon. Lastly, the expression of these PTS mediated-sugar utilization operons are often modulated by transcription regulators that contain duplicated PTS-regulatory domains (PRDs) (Stulke et al., 1998; van Tilbeurgh and Declerck, 2001). The phosphorylated level of PRDs by the PTS-mediated sugar transporter EIIB or HPr has been known to enable the sequential utilization of PTS-mediated sugar (Graille et al., 2005). Therefore, the change of carbon source preference by the deletion of the scrR gene in E. aerogenes might be triggered by PRDs. Future work will be directed towards clarifying the specific molecular mechanisms which are involved in determining the preferred carbon source in the mutant.

TABLE 5

| Strains | Wild type KCTC 2190 | EMY-01 | EMY-68 |
|---|---|---|---|
| Concentration of initial sugars (g/l) | 79.84 | 85.46 | 86.43 |
| Consumption of sugars (g/l) | 53.80 | 58.06 | 78.07 |
| 2,3-Butanediol (g/l) | 16.05 | 18.92 | 25.68 |
| 2,3-Butanediol productivity (g/l/h) | 1.33 | 1.58 | 2.14 |
| 2,3-Butanediol yield (g/g sugars) | 0.298 | 0.326 | 0.329 |
| Acetoin (g/l) | 1.21 | 1.53 | 0.57 |
| Lactate (g/L) | 1.73 | 0.01 | 0.02 |
| Ethanol (g/l) | 4.41 | 5.22 | 7.15 |
| Succinate (g/l) | 1.06 | 1.46 | 1.39 |

2.3 Fed-Batch Fermentation with EMY-68 Using Sugarcane Molasses

Figure 4:
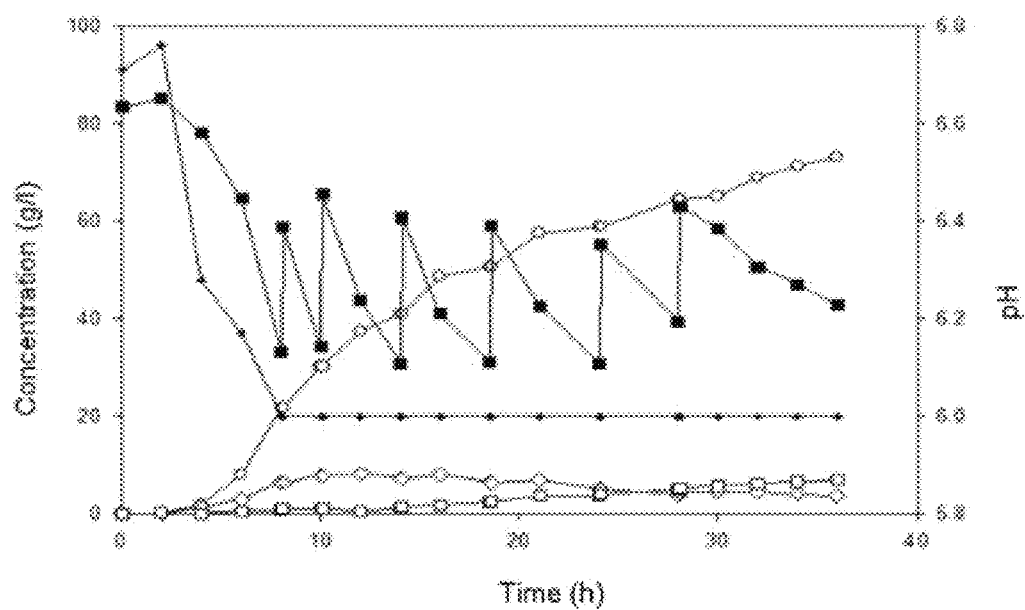
FIG. 4 shows graph for results of fed-batch fermentation using sugarcane molasses with pH (pluses), concentrations of 2,3-butanediol (open circles), ethanol (open diamonds), acetoin (open squares), and total sugars (closed squares).
Figure 5:
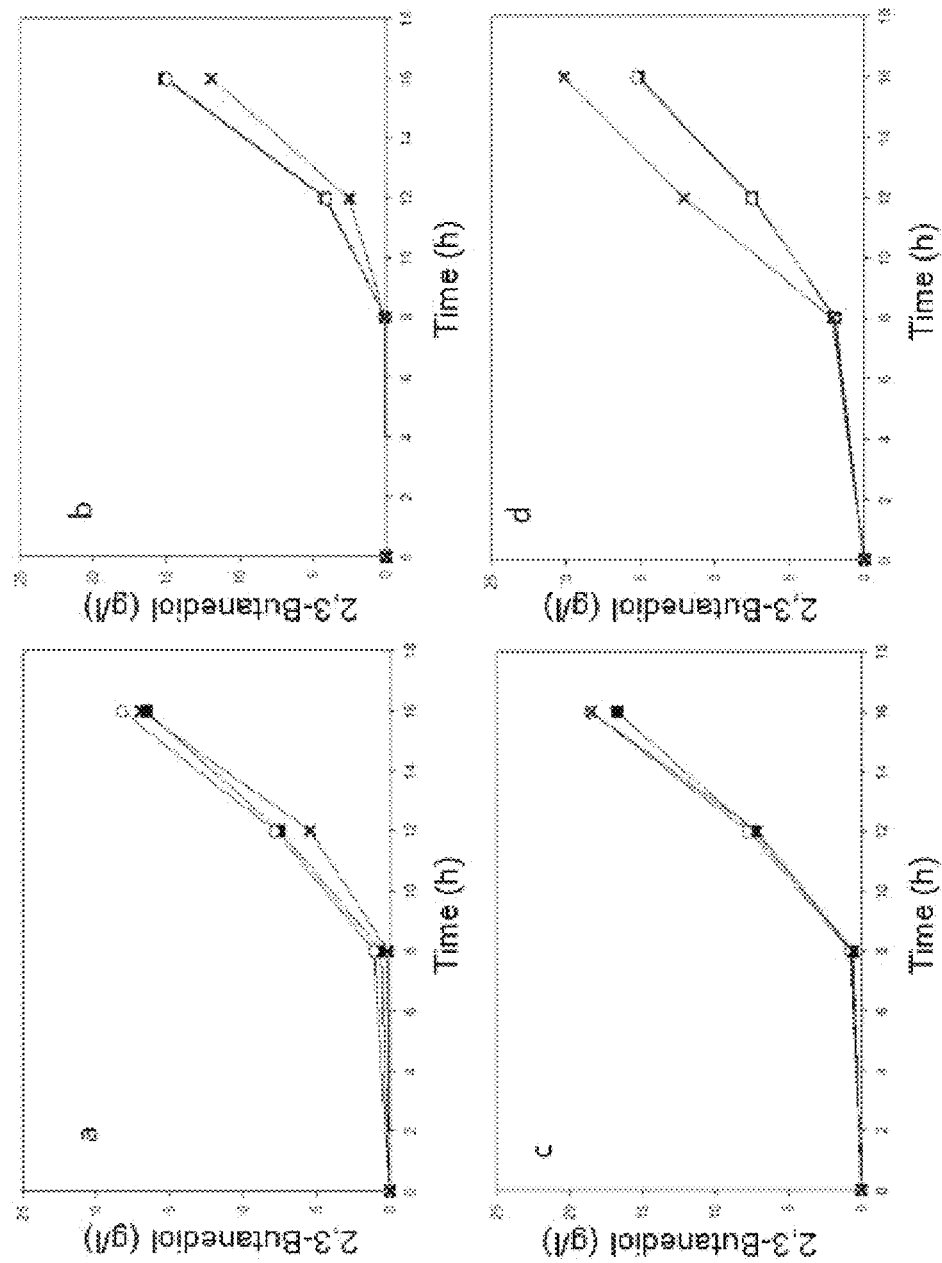
FIGS. 5a to 5d illustrate results showing 2,3-butanediol productions by KMK-01 (closed quadrangle), KMK-02 (open circle), and KMK-08 (X mark).
Figure 6:
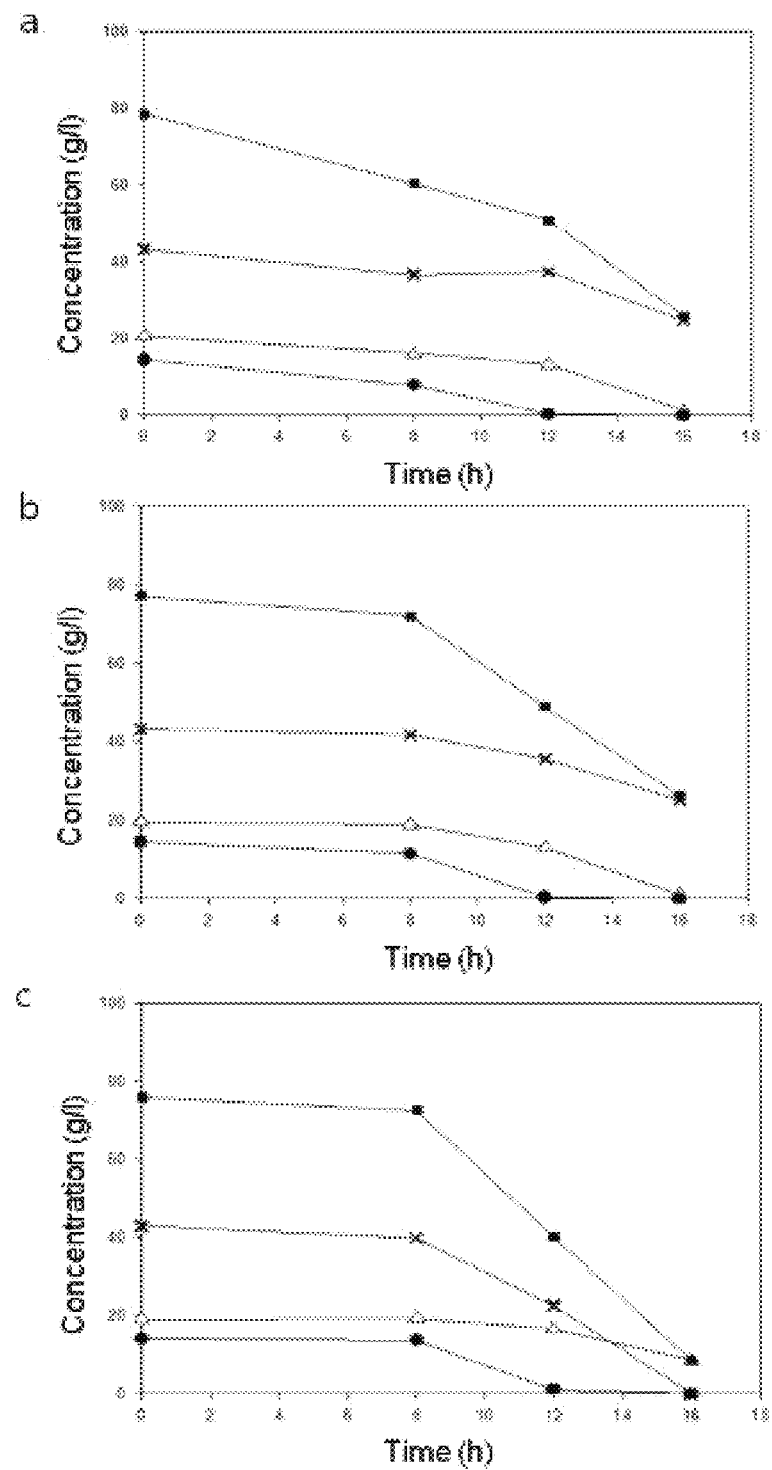
FIGS. 6a to 6c show carbon source consumption tendency results with respect to glucose (closed circle), sucrose (X mark), fructose (open triangle), and total carbon source (closed quadrangle) by KMK-01 (FIG. 6a), KMK-02 (FIG. 6b), and KMK-08 (FIG. 6c).

To further enhance 2,3-butanediol production from sugarcane molasses by EMY-68, a fed-batch fermentation with molasses feeding was performed. As shown in FIG. 4 and 202.89 g/L of sugars in sugarcane molasses was consumed and 2,3-butanediol production reached 72.89 g/L at 36 h of cultivation. The 2,3-butanediol yield and productivity were 0.359 g/g sugars and 2.02 g/L/h, respectively. Among the major byproducts, succinate was difficult to measure quantitatively, because its retention time in HPLC analysis was overlapped by an unknown substance of sugarcane molasses.

A very small amount of lactate was produced due to the deletion of lactate dehydrogenase. Meanwhile, maximum 7.89 g/L ethanol was produced until 16 h of cultivation, and as a primary metabolite, ethanol was produced during the logarithmic growth phase, and then was evaporated by relatively high temperature of fermentation (37° C.).

Example 2: 2,3-Butanediol Production Using *Klebsiella pneumonia*

1. Experimental Materials & Methods
1.1 Strain Development

The results with respect to the increase in the practical use of sucrose and molasses and the resultant increase in the production of 2,3-butanediol, through the removal of lactate dehydrogenase (LdhA) and sucrose regulator (ScrR) in the *Enterobacter aerogenes* KCTC 2190 strain, were applied to the *Klebsiella pneumonia* KCTC 2242 strain. The *Klebsiella pneumonia* strain is a representative 2,3-butanediol producing strain that is present in nature, together with *Enterobacter aerogenes*. The *Klebsiella pneumonia* strain has genes capable of using sucrose, and such genes have an operon (ScrA, EII transport protein for sucrose; ScrB, sucrose-6-phosphate hydrolase; ScrK, fructokinase; ScrY, outer membrane sucrose porin) In addition, *Klebsiella pneumonia* has scrR gene that regulates the expression of the operon. Therefore, in order to increase the rate of utilization of sucrose and molasses in the *Klebsiella pneumonia* strain, scrR was deleted by the A Red recombination method. In addition, in order to reduce the production of lactate, which is a main byproduct, and prevent the acidification of medium, lactate dehydrogenase was removed by the same method. Last, the *Klebsiella pneumonia* strain is a pathogen pertaining to class 2, and thus has a limitation in its industrial utilization. Since pathogenicity is known to occur by extracellular capsules, the wabG gene associated with the formation of the extracellular capsules was removed by the same method. Therefore, a total of three mutation strains were developed from the *Klebsiella pneumonia* strain. *Klebsiella pneumonia* (ΔwabG), *Klebsiella pneumonia* (ΔwabG ΔldhA), and *Klebsiella pneumonia* (ΔwabGΔldhAΔscrR) were named KMK-01, KMK-02, and KMK-03, respectively, and then the comparison test was conducted for the use of sucrose and molasses thereof and the production of 2,3-butanediol.

1.2. Media and Culture Condition

The *Klebsiella pneumonia* mutation strain was cultured in the same conditions of the "culture medium and culture condition" in example 1 above.

2. Results

*Klebsiella pneumonia* strain, KMK-08 without IdhA, scrR, and wabG through removal showed the decrease tendency by about 10% in the 2,3-butanediol production compared with the parent strain, when using glucose or fructose as a sole carbon source. However, the strain produced almost the same level of 2,3-butanediol compared with the parent strain when sucrose was given as a carbon source, and showed the increase by about 32% in the 2,3-butanediol productivity compared with the parent strain when molasses was a carbon source.

All the *Klebsiella pneumonia* strains (KMK-01, KMK-02, and KMK-08) consume three kinds of carbon sources at the same time. In KMK-01 and KMK-02, the consumption rate of glucose was the highest and the consumption rates of sucrose and fructose were almost similar to each other. However, in KMK-08, the consumption rate of sucrose was verified to be significantly increased compared with the consumption rate of fructose.

3. Conclusion

For the production of 2,3-butanediol, metabolically engineered *Enterobacter aerogenes* KCTC 2190 and *Klebsiella pneumonia* were cultured while sugar-cane molasses was used as a carbon source. When IdhA- and scrR-deleted *Enterobacter aerogenes* was subjected to fed-batch fermentation using sugar-cane molasses as a carbon source, the strain exhibited the 2,3-butanediol production of 72.89 g/L and sugar efficiency of 0.36 g/g of sugar for 36 h, and when IdhA, scrR, and wabG-deleted *Klebsiella pneumonia* was fermented using sugar-cane molasses as a carbon source, the strain exhibited the increase by 30% or more in the 2,3-butanediol production compared with those of scrR-non-deleted *Klebsiella pneumonia* (ΔldhA or ΔldhAΔwabG). Therefore, sucrose and sugar-cane molasses could be converted into 2,3-butanediol more efficiently by removing the transcriptional suppressor of the sucrose-using operon. These results suggest that the metabolically engineered strains can be 2,3-butanediol producing strains using economical carbon sources.

REFERENCES

Akaraonye, E., Moreno, C., Knowles, J. C., Keshavarz, T., Roy, I. 2012. Poly(3-hydroxybutyrate) production by *Bacillus cereus* SPV using sugarcane molasses as the main carbon source. Biotechnol J, 7(2), 293-303.

Arifin, Y, Sabri, S., Sugiarto, H., Kromer, J. O., Vickers, C. E., Nielsen, L. K. 2011. Deletion of cscR in *Escherichia coli* W improves growth and poly-3-hydroxybutyrate (PHB) production from sucrose in fed batch culture. J Biotechnol, 156(4), 275-278.

Bockmann, J., Heuel, H., Lengeler, J. W. 1992. Characterization of a chromosomally encoded, non-PTS metabolic pathway for sucrose utilization in *Escherichia coli* Ec3132. Mol Gen Genet, 235(1), 22-32.

Bruckner, R., Titgemeyer, F. 2002. Carbon catabolite repression in bacteria: choice of the carbon source and auto-regulatory limitation of sugar utilization. FEMS Microbiol Lett, 209(2), 141-148.

Chan, S., Kanchanatawee, S., Jantama, K. 2012. Production of succinic acid from sucrose and sugarcane molasses by metabolically engineered *Escherichia coli*. Bioresource Technol, 103(1), 329-336.

Datsenko, K. A., Wanner, B. L. 2000. One-step inactivation of chromosomal genes in *Escherichia coli* K-12 using PCR products. Proc Natl Acad Sci USA, 97(12), 6640-6645.

Ferenci, T., Kornberg, H. L. 1973. Utilization of fructose by *Escherichia coli*-Properties of a mutant defective in fructose-1-phosphate-kinase-activity. Biochem J, 132(2), 341-347.

Goerke, B., Stulke, J. 2008. Carbon catabolite repression in bacteria: many ways to make the most out of nutrients. Nat Rev Microbiol, 6(8), 613-624.

Graille, M., Zhou, C. Z., Receveur-Brechot, V., Collinet, B., Declerck, N., van Tilbeurgh, H. 2005. Activation of the LicT transcriptional antiterminator involves a domain swing/lock mechanism provoking massive structural changes. J Biol Chem, 280(15), 14780-14789.

Jahreis, K., Lengeler, J. W. 1993. Molecular analysis of two ScrR repressors and of a ScrR-FruR hybrid repressor for sucrose and D-fructose specific regulons from enteric bacteria. Mol Microbiol, 9(1), 195-209

Ji, X. J., Huang, H., Ouyang, P. K. 2011. Microbial 2,3-butanediol production: A state-of-the-art review. Biotechnol Adv, 29(3), 351-364.

Jiang, L. Q., Fang, Z., Guo, F., Yang, L. B. 2012. Production of 2,3-butanediol from acid hydrolysates of Jatropha hulls with *Klebsiella oxytoca*. Bioresource Technol, 107, 405-410.

Jung, M. Y., Ng, C. Y., Song, H., Lee, J., Oh, M. K. 2012. Deletion of lactate dehydrogenase in *Enterobacter aerogenes* to enhance 2,3-butanediol production. Appl Microbiol Biotechnol, 95(2), 461-469.

Kelker, N. E., Hanson, T. E., Anderson, R. L. 1970. Alternate pathways of D-fructose metabolism in Aerobacter *aerogenes-a* specific D-fructokinase and its preferential role in metabolism of sucrose. J Biol Chem, 245(8), 2060-&.

Ma, C. Q., Wang, A. L., Qin, J. Y., Li, L. X., Ai, X. L., Jiang, T. Y., Tang, H. Z., Xu, P. 2009. Enhanced 2,3-butanediol production by *Klebsiella pneumoniae* SDM. Appl Microbiol Biotechnol, 82(1), 49-57.

Mortlock, R. P. 1982. Regulatory mutations and the development of new metabolic pathways by bacteria. Evol Biol, 14, 205-268.

Reid, S. J., Abratt, V. R. 2005. Sucrose utilisation in bacteria: genetic organisation and regulation. Appl Microbiol Biotechnol, 67(3), 312-321.

Saier, M. H., Ramseier, T. M. 1996. The catabolite repressor/activator (Cra) protein of enteric bacteria. J Bacteriol, 178(12), 3411-3417.

Shiloach, J., Fass, R. 2005. Growing *E. coli* to high cell density—A historical perspective on method development. Biotechnol Adv, 23(5), 345-357.

Shin, S. H., Kim, S., Kim, J. Y., Lee, S., Um, Y, Oh, M. K., Kim, Y. R., Lee, J., Yang, K. S. 2012. Complete genome sequence of *Enterobacter aerogenes* KCTC 2190. J Bacteriol, 194(9), 2373-2374.

Sprenger, G. A., Lengeler, J. W. 1988. Analysis of sucrose catabolism in *Klebsiella Pneumoniae* and in Scr+ derivatives of *Escherichia coli* K12. J Gen Microbiol, 134, 1635-1644.

Stulke, J., Arnaud, M., Rapoport, G., Martin-Verstraete, I. 1998. PRD—a protein domain involved in PTS-dependent induction and carbon catabolite repression of catabolic operons in bacteria. Mol Microbiol, 28(5), 865-874.

Stulke, J., Hillen, W. 1999. Carbon catabolite repression in bacteria. Curr Opin Microbiol, 2(2), 195-201.

Sun, L. H., Wang, X. D., Dai, J. Y., Xiu, Z. L. 2009. Microbial production of 2,3-butanediol from Jerusalem artichoke tubers by *Klebsiella pneumoniae*. Appl Microbiol Biotechnol, 82(5), 847-852.

van Tilbeurgh, H., Declerck, N. 2001. Structural insights into the regulation of bacterial signalling proteins containing PRDs. Curr Opin Struc Biol, 11(6), 685-693.

Vertes, A. A. 2010. Biomass to biofuels: strategies for global industries. Wiley, Hoboken, N. J.

Wang, A. L., Wang, Y, Jiang, T. Y., Li, L. X., Ma, C. Q., Xu, P. 2010. Production of 2,3-butanediol from corncob molasses, a waste by-product in xylitol production. Appl Microbiol Biotechnol, 87(3), 965-970.

Zhang, L. Y., Sun, J. A., Hao, Y. L., Zhu, J. W., Chu, J., Wei, D. Z., Shen, Y. L. 2010. Microbial production of 2,3-butanediol by a surfactant (serrawettin)-deficient mutant of Serratia marcescens H30. J Ind Microbiol Biotechnol, 37(8), 857-862.

Features and advantages of the present invention are summarized as follows:

(a) The present invention provides a strain for producing 2,3-butanediol.

(b) The present invention can economically produce 2,3-butanediol by using a cheap carbon source.

(c) The present invention shows superior 2,3-butanediol efficiency and productivity compared with wild-type strains.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

REFERENCE TO A SEQUENCE LISTING

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A recombinant strain for producing 2,3-butanediol, comprising (a) a deletion of the strain's endogenous lactate dehydrogenase gene (IdhA), and (b) a deletion of the strain's endogenous sucrose regulator gene (scrR), such that the endogenous lactate dehydrogenase and the endogenous sucrose regulator are inactivated,
   wherein the sucrose regulator is a transcriptional suppressor that suppresses the expression of sucrose-6-phosphate hydrolase (ScrB),
   and
   wherein the strain is *Enterbacter aerogenes* or *Klebsiella pneumonia*.

2. The recombinant strain of claim 1, wherein the recombinant strain has a deletion, substitution, or insertion mutation further occurring in the nucleotide sequence encoding wabG.

3. The recombinant strain of claim 1, wherein the strain uses molasses as a carbon source.

4. A method for producing 2,3-butanediol, the method comprising culturing the strain of claim 1 in a culture medium.

5. The method of claim 4, wherein the culture medium contains molasses as a carbon source.

6. The method of claim 4, wherein the culture medium has an optimal pH range of pH 5.5 to pH 7.0.

7. The method of claim 4, wherein the culturing is performed by batch fermentation or fed-batch fermentation.

* * * * *

SEQUENCE LISTING

```
<160> NUMBER OF SEQ ID NOS: 6

<210> SEQ ID NO 1
<211> LENGTH: 990
<212> TYPE: DNA
<213> ORGANISM: Enterobacter aerogenes
<223> OTHER INFORMATION: lactate dehydrogenase

<400> SEQUENCE: 1
atgaaaatcg ctgtttatag taccaagcag tacgataaaa agtatctgca gcatgttaac      60
gacgcatacg gctttgaact ggaattttc gatttcctgc tgaccgaaaa gaccgcgaaa     120
acggccaacg gctgtgaagc ggtatgtatc ttcgttaatg acgacggtag ccgcccggtg     180
ctggaagagc taaaagccca cggcgtgaaa tatatcgcgc tgcgctgcgc cggctttaac     240
aacgtcgatc ttgaggcggc taaagagctg ggcctgcgcg tcgtgcgcgt cccggcctac     300
tcgccggaag ccgttgctga acacgccatc ggtatgatga tgtcgttgaa ccgtcgcatt     360
catcgcgcct atcagcgtac ccgcgatgcc aacttctcgc tggaagggct gaccggcttc     420
acgatgtacg gtaaaaccgc aggggtgatc ggcaccggta aaatcggcgt tgcgacgctg     480
cggatcctca aaggtttcgg tatgcgcctg ctggcgtttg atccctatcc gagcgcggcg     540
gcgctggatc tcggcgttga atatgtcgac ctgccgacgc tgtacgcgca gtccgacgtc     600
atctccctgc actgcccgct taccaacgaa aactatcacc tgctcaacca ggcggcattc     660
gatcagatga aagacggcgt gatggtcatt aataccagcc gcggcgcgct tatcgattca     720
caagcggcta tcgacgcgct gaagcatcag aaaatcggcg cgctgggaat ggacgtgtat     780
gaaaatgaac gcgatctgtt ctttgaagat aaatcgaatg atgtcatcca ggatgacgtg     840
ttccgccggc tctccgcctg ccacaacgtc ctgtttaccg ggcaccaggc attcctgacg     900
gctgaggcgc tgatcggtat ttccgagaca acgcttggca atctgcagca ggtagctaag     960
ggcgaaacct gcccgaacgc gctggtctaa                                      990

<210> SEQ ID NO 2
<211> LENGTH: 1014
<212> TYPE: DNA
<213> ORGANISM: Enterobacter aerogenes
<223> OTHER INFORMATION: sucrose regulator

<400> SEQUENCE: 2
atgaaaccta aacgcattac cattaaagat atcgccgaac tggctggcgt ctctaaagcc      60
accgccagcc tggtcttgaa cggtcgcggt aaagagctgc gcgtggcgca ggagacgcgc     120
```

-continued

```
gaacgggtgc tggctatcgc ccacgagcag cactaccagc cgagtattca cgcccgttca      180
ctgcgcgata gccgcagcca taccattggt ctggttgtgc cagagatcac caactatggt      240
tttgccgtgt tttctcacga gctggaaacc ctgtgccgcg aagccggcgt acagctgctt      300
atctcttgca ccgatgagaa tcccggtcag gagagcatgg tggtcaataa tatgattgcc      360
cgtcaggtcg atggtttaat tgtcgcctct tgcatgcata gcgacgccga ctatctgaag      420
ctcagcgagc agctgccggt ggtgctgttc gaccgtaatc caaacgacag cgcgctgccg      480
ctggtgatga ccgattcact ggcgccgacg gcggaactta tcgcccgtat cgccgggcaa      540
catgcggatg agttctggtt tctcggcggg cagccccggc tctcgccctc gcgcgatcgg      600
ctggccggat ttagtcaggg attagcccag gcaggggttg agttacgccc ggaatggatc      660
atcaacggca actatcaccc aagctcaggc tatgagatgt tgccgcgct gtgcgcccgc       720 ctcgggcggc cgcctaaggc gctgtttacc gccgcctgcg gcttgctgga aggggtacta     780
cgttatatga gccagcataa cctgctggat tccgggatcc atttagccag cttcgatgac     840
cactatctgt atgattcgct atcgctgcgc atcgacacca tccagcagga taaccgccag    900
ttggcctggc actgctacga tctcattagt cagttgatcg acggtaaaac gccacagccg     960
ctacagcgct atctgcccgc cacgctgcaa atgcgttatc agccagccag ataa         1014

<210> SEQ ID NO 3
<211> LENGTH: 70
<212> TYPE: DNA
<213> ORGANISM: Artificial Sequence
<220> FEATURE:
<223> OTHER INFORMATION: Primer scrR_FKF_fw

<400> SEQUENCE: 3
cggccatgca tggtagaata agcgttttgc tttcaggcgc ctgtctcgtg gtgtaggctg       60
gagctgcttc                                                            70

<210> SEQ ID NO 4
<211> LENGTH: 70
<212> TYPE: DNA
<213> ORGANISM: Artificial Sequence
<220> FEATURE:
<223> OTHER INFORMATION: Primer scrR_FKF_rv

<400> SEQUENCE: 4
gacaattaac cgttaacagt acgggcctga accacgatcc aggcccgtta tcctccttag     60
ttcctattcc                                                            70

<210> SEQ ID NO 5
<211> LENGTH: 19
<212> TYPE: DNA
<213> ORGANISM: Artificial Sequence
<220> FEATURE:
<223> OTHER INFORMATION: Primer scrR_con_A

<400> SEQUENCE: 5
ccgcttcttt gcggattat                                                  19

<210> SEQ ID NO 6
<211> LENGTH: 21
<212> TYPE: DNA
<213> ORGANISM: Artificial Sequence
```

```
<220> FEATURE:
<223> OTHER INFORMATION: Primer scrR_con_B

<400> SEQUENCE: 6
gcgctcattc atgaaaaatt c                                                    21
```